(12) United States Patent
Vu et al.

(10) Patent No.: US 11,001,548 B1
(45) Date of Patent: May 11, 2021

(54) METHOD OF PRODUCING ACETONE WITH LOW ALDEHYDES CONTENT

(71) Applicants: Truc Van Vu, Houston, TX (US); Eric Wing-Tak Wong, Houston, TX (US)

(72) Inventors: Truc Van Vu, Houston, TX (US); Eric Wing-Tak Wong, Houston, TX (US)

(73) Assignee: Kellogg Brown & Root LLC, Houston, TX (US)

(*) Notice: Subject to any disclaimer, the term of this patent is extended or adjusted under 35 U.S.C. 154(b) by 0 days.

(21) Appl. No.: 16/932,244

(22) Filed: Jul. 17, 2020

(51) Int. Cl.
*C07C 45/79* (2006.01)
*C07C 45/53* (2006.01)

(52) U.S. Cl.
CPC .................... *C07C 45/79* (2013.01)

(58) Field of Classification Search
CPC .................. C07C 45/79; C07C 45/53
See application file for complete search history.

(56) References Cited

U.S. PATENT DOCUMENTS

| 4,340,447 A | 7/1982 | Laverick et al. |
| 5,777,180 A | 7/1998 | June et al. |

*Primary Examiner* — Sikarl A Witherspoon
(74) *Attorney, Agent, or Firm* — Gary M. Machetta

(57) ABSTRACT

Methods and systems for preparing acetone from cumene hydroperoxide (CHP) are disclosed. The methods and systems involve an acetone purification column configured to separate acetone from other components of the product/reactant stream. The acetone purification column is equipped with a side draw configured to route a portion of the column contents to a caustic treating vessel where the contents are reacted with a dilute aqueous alkaline solution to remove aldehydes from the acetone product. The contents of the caustic treating vessel are then routed back to the acetone purification column. Using a separate caustic treating vessel for the aldehydes removal provides increased contact time between the acetone product and the alkaline solution, thereby affording greater aldehydes removal.

24 Claims, 4 Drawing Sheets

METHOD OF PRODUCING ACETONE WITH LOW ALDEHYDES CONTENT

FIELD OF THE INVENTION

This application relates to methods and systems for producing acetone from cumene. More specifically, embodiments relate to improving the purity of the produced acetone.

INTRODUCTION

Phenol and acetone are produced in various processes, the most common of which is known variously as the Hock Process, the Hock and Lang Process, or the cumene-to-phenol process, among others. This process begins with the oxidation of cumene (isopropyl benzene) to form cumene hydro-peroxide (CHP). The CHP is then cleaved in the presence of an acid catalyst to form a phenol, acetone, and/or alpha-methyl styrene ("AMS") mixture. The mixture is subsequently neutralized and fractionated to recover the end-products phenol, acetone, and/or AMS.

While such processes have been used for decades, there is a continued need for optimizing the purity of the produced aldehydes.

SUMMARY

Disclosed herein is a method of purifying acetone in an acetone production process, the method comprising: feeding a crude acetone fraction to a first feed point in an acetone purification column (APC), removing a portion of the crude acetone fraction from the APC via a first side draw of the APC located above the first feed point, feeding the removed portion of the crude acetone fraction to a caustic treating vessel, feeding an aqueous alkaline solution to the caustic treating vessel, returning a bottoms stream from the caustic treating vessel to the APC via a second feed point, wherein the second feed point is located between the first feed point and the first side draw, and obtaining purified acetone from a second side draw located above first side draw. According to some embodiments, the crude acetone fraction is obtained as an overhead stream from a crude acetone column (CAC) upstream of the APC. According to some embodiments, the crude acetone fraction comprises acetone, water, cumene, alpha-methyl styrene (AMS), phenol, methanol, and aldehydes. According to some embodiments, the crude acetone fraction comprises 60 to 1000 ppm (vol) aldehydes, and wherein the aldehydes comprise acetaldehyde and/or propionaldehyde. According to some embodiments, the crude acetone fraction comprises 50 to 500 ppm (vol) methanol. According to some embodiments, the aqueous alkaline solution comprises an alkali or alkaline earth metal oxide, hydroxide, or phenate. According to some embodiments, the aqueous alkaline solution comprises sodium hydroxide. According to some embodiments, the sodium hydroxide has a concentration of about 0.1 to about 15%. According to some embodiments, the caustic treating vessel has a temperature of about 45 to about 75° C. According to some embodiments, the caustic treating vessel comprises no internals. According to some embodiments, the caustic treating vessel comprises static mixing internals. According to some embodiments, the caustic treating vessel comprises an agitator. According to some embodiments, the caustic treating vessel comprises a circulation pump. According to some embodiments, the caustic treating vessel provides a residence time of about 3 to about 60 minutes. According to some embodiments, the method further comprises contacting the removed portion of the crude acetone fraction with a zeolite adsorbent to remove methanol from the removed portion of the crude acetone fraction before feeding it to the caustic treating vessel. According to some embodiments, the purified acetone comprises total aldehydes of less than about 20 ppmwt. According to some embodiments, the purified acetone has a permanganate time of greater than 12 hours. According to some embodiments, the purified acetone has a methanol content of less than 100 ppm (wt).

Also disclosed herein is a system for recovery of purified acetone, the system comprising: a crude acetone column (CAC) configured to separate products of a cumene hydroperoxide cleavage reaction into an overhead fraction comprising crude acetone and a bottom fraction comprising phenol, an acetone purification column (APC) configured to: receive the crude acetone at a first feed point in the APC, separate the crude acetone into purified acetone and residual heavy compounds, and provide the purified acetone at a first side draw located above the first feed point, and a caustic treating vessel configured to: receive a portion of the crude acetone drawn from a second side draw of the APC located above the first feed point and below the first side draw of the APC, receive a feed of aqueous alkaline solution, mix the portion of the crude acetone and the aqueous alkaline solution, and return contents of the caustic treating vessel to a second feed point of the APC, wherein the second feed point is located between the first feed point and the second side draw. According to some embodiments, the crude acetone fraction comprises acetone, water, cumene, alpha-methyl styrene (AMS), phenol, methanol, and aldehydes. According to some embodiments, the aqueous alkaline solution comprises sodium hydroxide. According to some embodiments, the caustic treating vessel provides a residence time of about 3 to about 60 minutes. According to some embodiments, the caustic treating vessel is without any internals. According to some embodiments, the caustic treating vessel comprises one or more of static mixing internals, an agitator, or a circulation pump.

DETAILED DESCRIPTION

Figure 1:
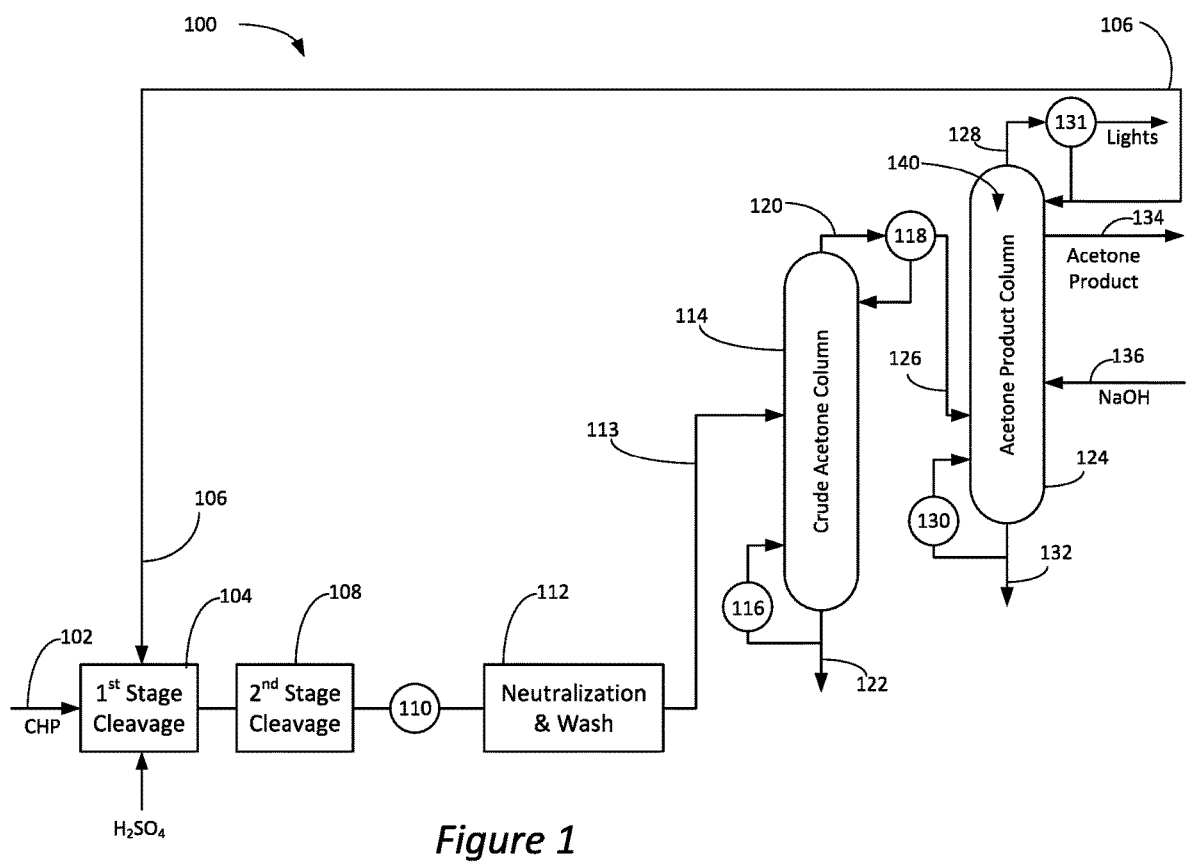
FIG. 1 shows an embodiment of a system for producing acetone and phenol from cumene hydroperoxide (CHP).

FIG. 1 illustrates a system 100 for producing acetone and phenol from cumene hydroperoxide (CHP). It will be appreciated that some aspects and equipment of the system 100 (and the other systems described in this disclosure) that are not particularly relevant to this disclosure but that are implemented in the actual operation of such a system are not mentioned here. Such aspects and equipment are known in the art and may be described in the above-incorporated references.

Concentrated CHP enters the system via line 102. The concentration of the CHP in line 102 may be about 65-90 wt. %, and is more typically about 80-85 wt. %, for example to about 82 wt. %. The CHP may be produced by the oxidation of cumene, for example, as described in U.S. Pat. No. 8,697,917, the entire contents of which are incorporated herein by reference. The oxidation product from the cumene oxidation (not shown) comprises CHP and may also comprise one or more of alpha-methyl styrene (AMS), dimethyl benzyl alcohol (DMBA), and/or acetophenone (ACP).

The concentrated CHP is provided to one or two cleavage reactors in series, for example, as described in U.S. Pat. No. 5,371,305. In the illustrated system 100, two cleavage reactors in series are illustrated. The CHP is provided to a first cleavage reactor 104, where it undergoes acid-catalyzed cleavage. The acid catalyst may be sulfuric acid ($H_2SO_4$), for example. In the illustrated embodiment, the first cleavage reactor may be a back-mixed reactor, for example, and operate between 50° C. and 80° C. In the first cleavage reactor, CHP partially reacts in two reactions, i) CHP cleaved to form phenol and acetone, and ii) CHP partially reacts with DMBA in an equilibrium reaction to give an intermediate product dicumyl peroxide (DCP) and water. DMBA is partially dehydrated to AMS, which reacts in consecutive reactions with phenol to high-boiling cumylphenols, AMS can also form high-boiling point dimers. Additional byproducts can also produce, such as hydroxyacetone (HA), 2-methylbenzofurane (2-MBF), and mesityl oxide (MO). The cleavage reaction is highly exothermic thus, recycled acetone may be provided to the cleavage reactor(s) to maintain the proper dilution, thereby minimizing the formation of undesirable by-products. In the illustrated embodiment, recycled product acetone is provided to the first cleavage reactor via line 106. Water may also be added for optimum cleavage yields.

In the illustrated embodiment, the product of the first cleavage reactor 104 is fed to a second cleavage reactor 108 where three main reactions take place: i) residual CHP from first cleavage reactor cleaves to phenol and acetone, ii) dehydration of residual DMBA from first cleavage reactor to AMS, and iii) conversion of DCP to AMS, phenol, and acetone. The second stage cleavage reactor may be a plug flow reactor, for example, at temperatures about 105° C. to 145° C., and may be steam heated.

In the illustrated system 100, the cleavage product from the second cleavage reactor 108 is cooled using cooler 110 and directed to one or more neutralization and wash units 112. The cleavage effluent contains sulfuric acid used as catalyst for the cleavage reaction. To avoid corrosion problems in the downstream equipment, the acids must be extracted and neutralized using one or more bases, such as sodium hydroxide and/or one or more salt solutions. For example, the salt solution can be or include sodium phenate. The salt solution can reduce or stop any continuing cleavage reactions in the cleavage product. Accordingly, the neutralization and wash units 112 can produce a neutralized cleavage product.

The steps (i.e., acetone fractionation) following cleavage and neutralization are primarily aimed towards purification of products (acetone and phenol) and recovery of by-products and recyclable cumene. The acetone fractionation system serves the purpose of (1) crude separation of lights and heavies in the fractionation feed and (2) purification of acetone product. The organic effluent from the neutralization unit(s) 112 flows to a first distillation column via line 113. The first distillation column is referred to herein as the crude acetone column (CAC) 114. The function of the CAC is to split the neutralization product into a phenol fraction and an acetone fraction. Aspects of a CAC are described in U.S. Pat. No. 8,889,915, the entire contents of which are incorporated herein by reference. The vapor distillate (line 120) contains acetone, water, cumene, AMS, small amounts of phenol, and other light materials in the feed. The CAC may be equipped with a CAC reboiler 116 and a CAC condenser 118. The CAC reboiler 116 may be a forced circulation type exchanger heated by high-pressure steam, for example. The phenol-rich bottom material (line 122) may be directed to a phenol fractionation unit (not shown). The overhead vapor (line 120) is partially condensed in the CAC condenser 118. The condensed liquid is returned to the CAC 114, while the vapor distillate is sent to a second distillation column, referred to herein as the acetone product column or the acetone purification column (APC) 124 via line 126. According to some embodiments, the vapor distillate provided to the APC 124 via line 126 may comprise about 7 to about 12 vol % cumene, about 0.1 to about 0.2 vol % phenol, about 40 to about 50 vol % acetone, about 1 to about 2 vol % AMS, about 200 to about 500 ppm (vol) methanol, and about 100 to about 1000 ppm (vol) total aldehydes.

The purpose of the APC 124 is to remove light ends (primarily acetaldehyde, via line 128) from acetone product and to separate acetone from water, cumene, AMS, and other heavy organics. Aspects of an APC are described in U.S. Pat. No. 4,340,447 ("the '447 Patent), the contents of which are incorporated by reference. The APC is equipped with an APC reboiler 130 and an APC condenser 131. The APC reboiler 130 may be fed from a liquid trap out of the bottom tray of the APC 124 and a re-circulation stream from the bottom of the column, and may heated by low-pressure steam.

An interior volume 140 of the APC 124 can be empty, partially filled, or completely filled with one or more fill materials (not shown). Illustrative fill materials can include, but are not limited to, trays, packing, or combinations thereof. As used herein, the term "trays' can include, but is not limited to, one or more types of trays that can improve the contact between gas and liquid phases within APC 124. Illustrative trays can include, but are not limited to, perforated trays, sieve trays, bubble cap trays, floating valve trays, fixed valve trays, cartridge trays, dual flow trays, baffle trays, shower deck trays, chimney trays, slit trays, or any combination thereof. As used herein, the term "packing material' or "packing can include, but is not limited one or more types of structured and/or random shaped material disposed within APC 124. The packing material can increase the effective surface area within APC 124, which can improve the mass transfer between liquid and gas phases within APC 124. The packing material can be made of any suitable material, for example metals, non-metals, polymers, ceramics, glasses, or any combination thereof. Illustrative examples of random packing material can include, but is not limited to, Raschig rings, NeXRing™, Nutter Rings™, I-Rings™, C-Rings™, P-Rings™, R-Rings™ and S-Rings™, Intalox® ULTRA, IMTP®, HY-PAK, CASCADE MINI RINGS®, FLEXIRING®, AHPP Saddle-Rings, Pall rings, SuperBlend™ 2-Pac, or any combination thereof. Illustrative examples of commercially available structured packing can include, but is not limited to, structured packing, corrugated sheets, crimped sheets, gauzes, grids, wire mesh, or any combination thereof. The fill material, can improve mass transfer and/or separation of a multi-component fluid. The fill material and/or the fill pattern in the interior Volume 140 can include one or more structured and/or random packed materials. Two or more types of fill material can be disposed within the interior volume 126. The APC 124 can be made of one or more metallic materials physically and chemically compatible with the temperature, pressure, and contents of APC 124. Suitable metallic materials can include, but are not limited to ferrous alloys including carbon and stainless steels such as cladded carbon Steel and 304 and 316 stainless steels, and duplex stainless steel and combination of these metallic materials. Further, the APC 124 can be operated at a pressure temperature ranging from a low of about 40 kPa, about 50 kPa, or about 60 kPa, to a high of about 80 kPa, about 90 kPa, or about 100 kPa.

The net bottoms stream 132 from the APC 124 may be fed to a crude AMS was section (not shown). Product acetone may be obtained from a side draw 134. A portion of the APC 124 reflux may be recycled to the cleavage reactor section via line 106, for example, to the first cleavage reactor 104, as mentioned above. The amount of recycled acetone may be determined as a ratio based on the feed of CHP to the cleavage reactor. For example, the amount of acetone recycled to the cleavage reactor(s) may be about 0.1 to about 0.5 by weight based on the feed of CHP to the cleavage reactor(s).

The APC 124 is provided with a caustic addition points 136 for the addition of caustic material. The caustic material may be an alkali or alkaline earth metal oxide, hydroxide, or phenate, for example. One example of a suitable caustic material is sodium hydroxide. The caustic addition point 136 is provided between the feed stream 126 and the product side draw 134. The caustic is added to the APC 124 to reduce the amount of aldehyde in the acetone product. The aldehydes form heavy ketones in the presence of the caustic via an aldol condensation reaction, thereby purifying the acetone product. The use of caustic in the APC 124 to reduce the amount of aldehyde in the acetone product is described in the incorporated '447 Patent.

As is known in the art, one test for determining the purity of the acetone product is the permanganate time (PMT) test, which involves adding a small quantity of potassium permanganate to a sample of acetone and determining the time required for the color to dissipate. A longer color dissipation time (the PMT) indicates a lower content of reducing substances, such as aldehydes, in the sample and a higher quality of the acetone. The methods described in the '477 Patent can produce acetone having a PMT of about 4 hours, which corresponds to about 60 to about 120 ppm (vol) of total aldehyde impurity.

In embodiments as illustrated in FIG. 1 and as described in the '477 Patent, the extent to which aldehydes and other reducing substances are removed by reacting with the caustic material in the APC column is limited by the time that the caustic is in contact with the aldehydes inside the column. The aldol condensation relies on the contact time between the aldehydes and the caustic on the distillation trays of the APC. The residence time on the distillation trays may be short, for example a few minutes; thus, the aldol condensation of the aldehydes may not be completed and is strongly dependent on the operating throughput of the column.

Figure 2:
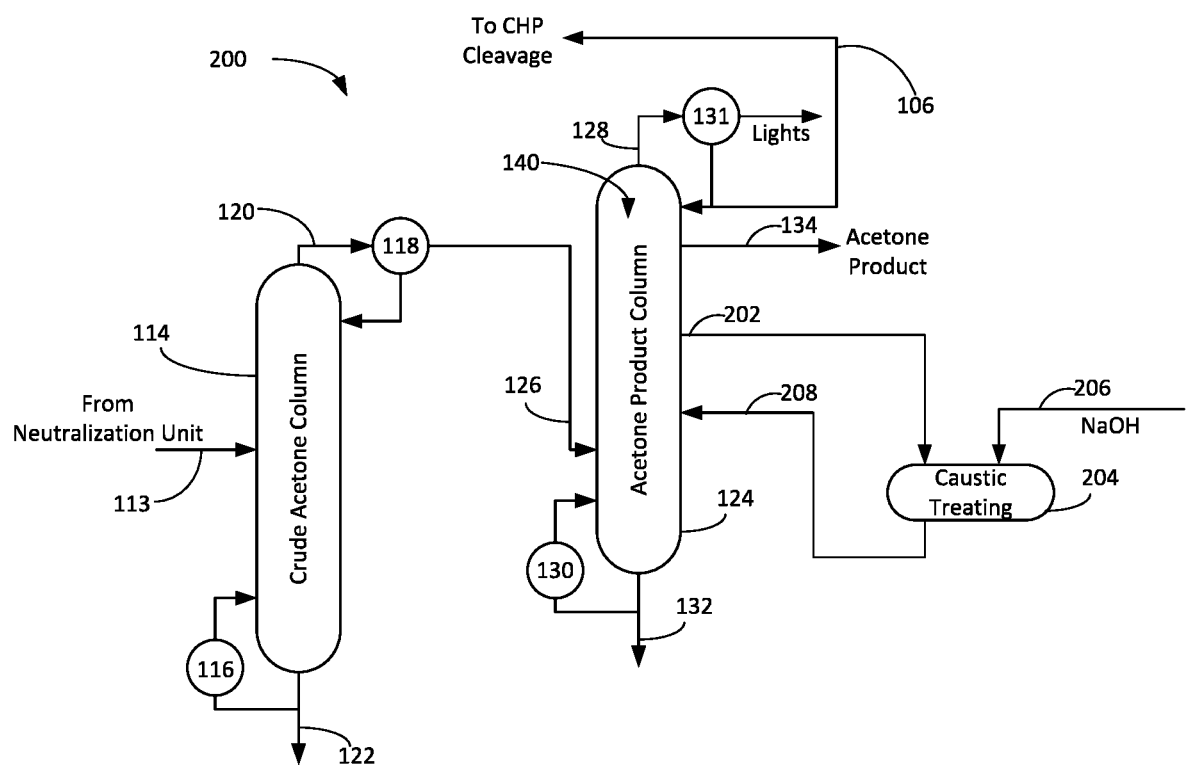
FIG. 2 shows an embodiment of an improved system for purifying acetone, wherein in a portion of the produced acetone is reacted with a caustic material within a caustic reaction vessel.

The inventors have realized that the contact time of the aldehydes with the caustic can be improved using a system 200, as illustrated in FIG. 2. In FIG. 2, like numbers represent like components to the system 100 illustrated in FIG. 1. FIG. 2 illustrates a CAC 114 and APC 124, both of which are similar to the corresponding equipment of system 100 (FIG. 1). The system 200 also includes the upstream equipment illustrated in FIG. 1, i.e., the cleavage reactors (104, 108), cooler (110), and the neutralization and wash units (112), but that equipment is omitted from FIG. 2 for clarity. As in the system 100 (FIG. 1), in the system 200 (FIG. 2) the organic effluent from the neutralization unit(s) flows to the CAC 114 via line 113. The vapor distillate (referred to herein as a "crude acetone fraction") from the CAC is provided to the APC 124 via line 126 and the phenol-rich bottom material exits the CAC via line 122. According to some embodiments, the crude acetone fraction provided to the APC 124 via line 126 may comprise about 12 vol % cumene, about 0.1 to about 0.2 vol % phenol, about 40 to about 50 vol % acetone, about 1 to about 2 vol % AMS, about 50 to about 500 ppm (vol) methanol, and about 60 to about 1000 ppm (vol) total aldehydes. More particularly, the crude acetone fraction may comprise about 60 to 1000 ppm (vol) aldehydes, wherein the aldehydes comprise acetaldehyde and/or propionaldehyde.

The interior volume 140 of the APC 124 of the system 200 is as described above. The APC 124 of the system 200 is equipped with a side draw 202 from which a portion of the material within the column can be obtained and provided to a caustic treating vessel 204. The side draw may be configured at any point on the APC 124, but according to most embodiments is configured between the inlet line 126 from the CAC and the acetone product line 134, as illustrated in FIG. 2. Caustic material is provided to the caustic treating vessel 204 via line 206. As in the system 100 (FIG. 1), the caustic material may be an alkali or alkaline earth metal oxide, hydroxide, or phenate, for example. One example of a suitable caustic material is sodium hydroxide. A bottoms stream from the caustic treating vessel 204 is returned to the APC 124 via line 208, which again, is typically configured to feed to the APC at a position between lines 126 and 134.

Removing a portion of the material from the APC and reacting it with the caustic material in the caustic treating vessel 204 before returning the contents of the caustic treating vessel to the APC increases the contact time with the caustic material. This results in more efficient aldehydes removal from the acetone product, compared to the system 100 (FIG. 1). System 200 is also capable of handling higher aldehydes content in the crude vapor acetone feed (i.e., the feed entering the APC via line 126). High levels of aldehydes may be due to: 1) high impurities in the cumene feedstock to the plant, and/or 2) the presence of recycle acetone stream from other process units that use acetone downstream of the phenol plant. In system 200, the stream being caustic treated (i.e., stream 202) is free of phenol and has low levels of other organic impurities, such as cumene and AMS.

The caustic treating vessel 204 may be a vessel with no internals, for example. According to some embodiments, mixing may be provided in the caustic treating vessel 204, since the streams being combined are in two liquid phases. That is, stream 202 is an organic phase comprising primarily acetone, cumene, and AMS, and stream 206 is an aqueous phase. The mixing may be accomplished, for example, using static mixing-type internals installed inside the vessel, an agitator installed together with the vessel, and/or a circulation pump to promote mixing and contact of the two phases. According to some embodiments, the residence time of contents in the caustic treating vessel may be about 3 to about 60 minutes, for example about 5 to 30 minutes.

According to some embodiments, the concentration of the caustic in the caustic treating vessel 204 may be about 0.1 to about 15% caustic. According to some embodiments, the temperature within the caustic treating vessel is about 45 to about 75° C., for example 50 to 65° C. According to some embodiments, the temperature within the caustic treating vessel is maintained from the heat of the heat of the materials transferred from the APC and no additional heating is required. Alternatively, additional heat may be supplied to the caustic treating vessel, by steam heating, for example.

As mentioned above, the caustic-treated stream is returned to the APC via line 208, which may enter the APC immediately above the vapor feed line 126, for example. Phenol in the APC is converted to sodium phenate due to presence of free caustic in the caustic feed from the caustic treating vessel. Residual aldehydes are also converted to heavy ketones on the trays of the APC, together with the phenol/sodium phenate reaction. Other heavier organic impurities, such as cumene and AMS are removed from the acetone as the vapor progresses up the column.

The inventors have found that the disclosed methods and systems, such as system 200, can produce acetone having a total aldehydes content of about 5 to about 40 ppm (wt). According to some embodiments, the aldehydes content is less than 40 ppm (wt), less than 20 ppm (wt), or less than 10 ppm (wt). The resulting acetone can achieve a permanganate time of about 12 to about 24 hours, a significant improvement over the prior art systems. For example, according to some embodiments, the permanganate time is greater than 12 hours, greater than 18 hours, or greater than 24 hours.

Figure 3:
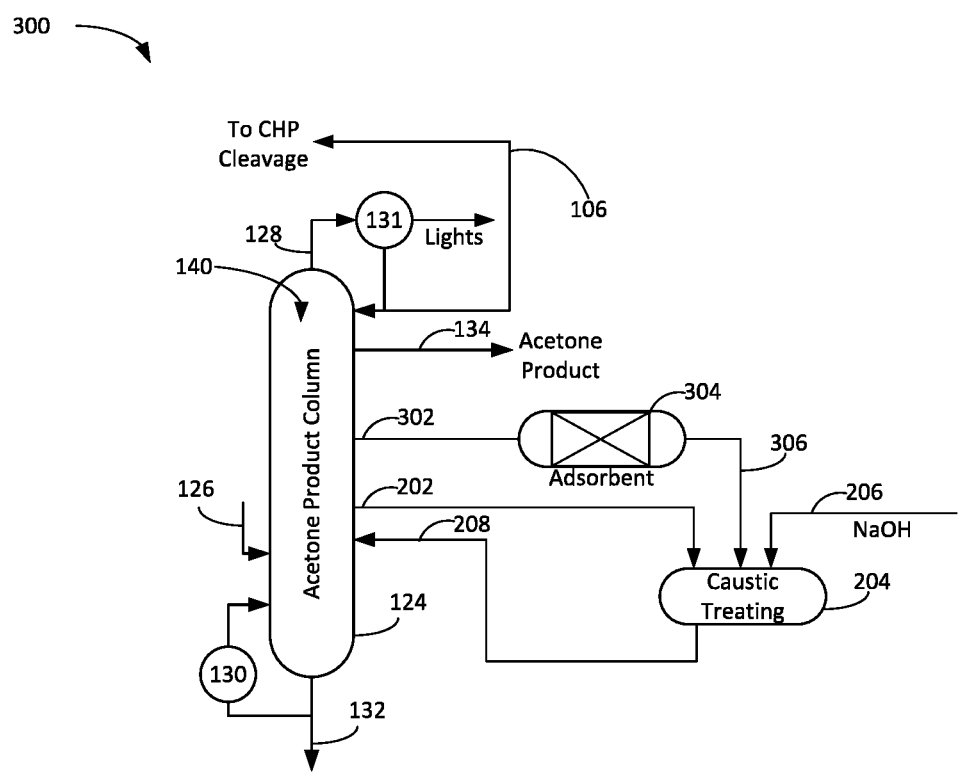
FIG. 3 shows an embodiment of an improved system for purifying acetone, wherein in a portion of the produced acetone is routed through an adsorbent vessel to remove alkyl alcohols from the produced acetone.
Figure 4:
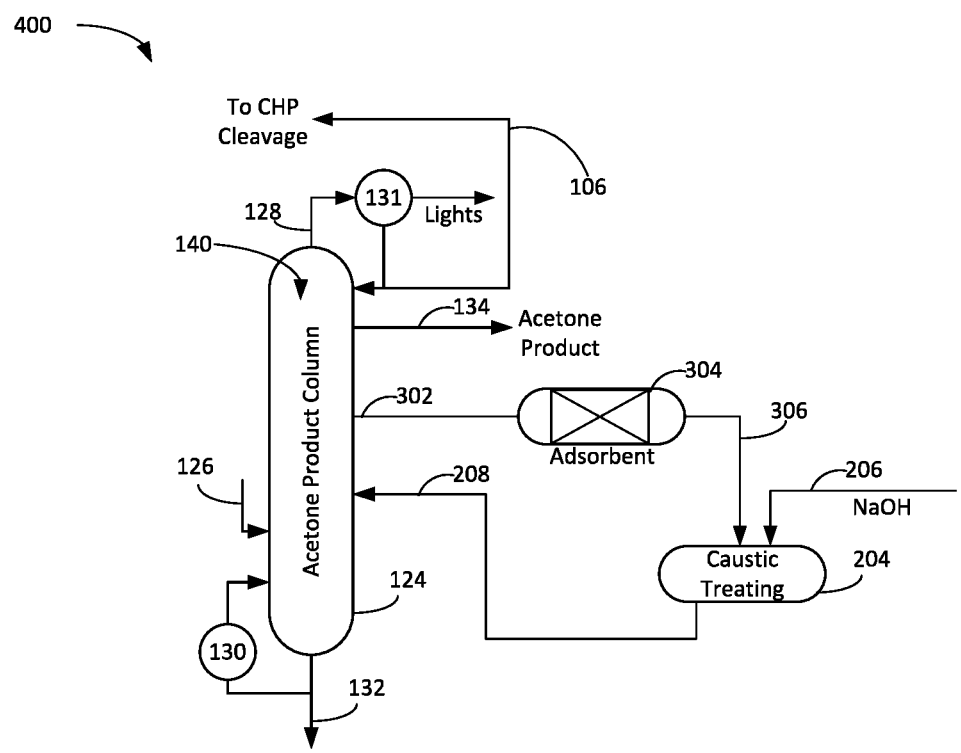
FIG. 4 shows a further embodiment of an improved system for purifying acetone, wherein in a portion of the produced acetone is routed through an adsorbent vessel to remove alkyl alcohols from the produced acetone.

FIGS. 3 and 4 show further embodiments for purifying acetone in an APC. In FIGS. 3 and 4, only the APC and associated equipment is illustrated. It should be appreciated that the systems 300 (FIG. 3) and 400 (FIG. 4) each include the upstream equipment illustrated in FIGS. 1 and 2, but that equipment is omitted from the FIGS. 3 and 4 for clarity. In FIGS. 3 and 4, like numbers represent like components to the systems 100 and 299 illustrated in FIGS. 1 and 2, respectively.

As illustrated in FIGS. 3 and 4, the inventors have realized that the acetone purified in the APC 140 can be further purified to remove alkyl alcohols, such as methanol, by routing a portion of the APC contents through an adsorbent, such as a zeolite, for example, molecular sieve material. Referring to FIG. 3, the APC 140 is equipped with a first side draw 202, which routes a portion of the APC contents to the caustic treating vessel 204, as in system 200 (FIG. 2). The APC 140 is also equipped with a further side draw 302, which routes a portion of the APC contents to an adsorbent vessel 304, which is configured to contain an adsorbent, such as zeolite molecular sieve material. Examples of suitable zeolite molecular sieve materials include molecular sieves having pore sizes of about 4 to about 5 A. The contents from the adsorbent vessel 304 are then provided to the caustic treating vessel 204 via line 306. Aldehydes are removed in the caustic treating vessel 204, as described above. The effluent stream from the caustic treating vessel is returned to the APC 140 via line 208, as described for system 200 (FIG. 2) above.

FIG. 4 illustrates an alternative embodiment of a system 400 having an APC 140 equipped with an adsorbent vessel 304 containing an adsorbent, such as molecular sieve material, for removing alkyl alcohols from the acetone. The system 400 differs from the system 300 (FIG. 3) in that all of the APC contents routed from the APC 140 to the caustic treating vessel 204 pass through the adsorbent vessel 304. In other words, a portion of the APC contents are directed to the adsorbent vessel 304 via line 302. The contents of the adsorbent vessel 304 are then directed to the caustic treating vessel 204 via line 306. There is no other side draw, such as side draw 202 (FIG. 3), for providing contents of the APC directly to caustic treating vessel 204. In other aspects, the systems 300 (FIG. 3) and 400 are the same. The inventors have found that systems, such as system 300 (FIG. 3) and system 400 (FIG. 4) can produce acetone that with aldehyde contents of less than 20 ppm (wt), or less than 10 ppm (wt); permanganate times of greater than 12 hours, greater than 18 hours, or greater than 24 hours, and methanol contents of less than 100 ppm (wt), or less than 50 ppm (wt).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of purifying acetone in an acetone production process, the method comprising:
   feeding a crude acetone fraction to a first feed point in an acetone purification column (APC),
   removing a portion of the crude acetone fraction from the APC via a first side draw of the APC located above the first feed point,
   feeding the removed portion of the crude acetone fraction to a caustic treating vessel,
   feeding an aqueous alkaline solution to the caustic treating vessel,
   returning a bottoms stream from the caustic treating vessel to the APC via a second feed point, wherein the second feed point is located between the first feed point and the first side draw, and
   obtaining purified acetone from a second side draw located above first side draw.

2. The method of claim 1, wherein the crude acetone fraction is obtained as an overhead stream from a crude acetone column (CAC) upstream of the APC.

3. The method of claim 1, wherein the crude acetone fraction comprises acetone, water, cumene, alpha-methyl styrene (AMS), phenol, methanol, and aldehydes.

4. The method of claim 1, where in the crude acetone fraction comprises 60 to 1000 ppm (vol) aldehydes, and wherein the aldehydes comprise acetaldehyde and/or propionaldehyde.

5. The method of claim 1, where in the crude acetone fraction comprises 50 to 500 ppm (vol) methanol.

6. The method of claim 1, wherein the aqueous alkaline solution comprises an alkali or alkaline earth metal oxide, hydroxide, or phenate.

7. The method of claim 4, wherein the aqueous alkaline solution comprises sodium hydroxide.

8. The method of claim 5, wherein the sodium hydroxide has a concentration of about 0.1 to about 15%.

9. The method of claim 1, wherein the caustic treating vessel has a temperature of about 45 to about 75° C.

10. The method of claim 1, wherein the caustic treating vessel comprises no internals.

11. The method of claim 1, wherein the caustic treating vessel comprises static mixing internals.

12. The method of claim 1, wherein the caustic treating vessel comprises an agitator.

13. The method of claim 1, wherein the caustic treating vessel comprises a circulation pump.

14. The method of claim 1, wherein the caustic treating vessel provides a residence time of about 3 to about 60 minutes.

15. The method of claim 1, further comprising contacting the removed portion of the crude acetone fraction with a zeolite adsorbent to remove methanol from the removed portion of the crude acetone fraction before feeding it to the caustic treating vessel.

16. The method of claim 1, wherein the purified acetone comprises total aldehydes of less than about 20 ppmwt.

17. The method of claim 1, wherein the purified acetone has a permanganate time of greater than 12 hours.

18. The method of claim 1, wherein the purified acetone has a methanol content of less than 100 ppm (wt).

19. A system for recovery of purified acetone, the system comprising:
   a crude acetone column (CAC) configured to separate products of a cumene hydroperoxide cleavage reaction into an overhead fraction comprising crude acetone and a bottom fraction comprising phenol,
   an acetone purification column (APC) configured to:
      receive the crude acetone at a first feed point in the APC,
      separate the crude acetone into purified acetone and residual heavy compounds, and
      provide the purified acetone at a first side draw located above the first feed point, and
   a caustic treating vessel configured to:
      receive a portion of the crude acetone drawn from a second side draw of the APC located above the first feed point and below the first side draw of the APC,
      receive a feed of aqueous alkaline solution,
      mix the portion of the crude acetone and the aqueous alkaline solution, and
      return contents of the caustic treating vessel to a second feed point of the APC, wherein the second feed point is located between the first feed point and the second side draw.

20. The system of claim 15, wherein the crude acetone fraction comprises acetone, water, cumene, alpha-methyl styrene (AMS), phenol, methanol, and aldehydes.

21. The system of claim 15, wherein the aqueous alkaline solution comprises sodium hydroxide.

22. The system of claim 15, wherein the caustic treating vessel provides a residence time of about 3 to about 60 minutes.

23. The system of claim 15, wherein the caustic treating vessel is without any internals.

24. The system of claim 15, wherein the caustic treating vessel comprises one or more of static mixing internals, an agitator, or a circulation pump.

* * * * *